United States Patent [19]

Chiodo et al.

[11] Patent Number: 4,844,095
[45] Date of Patent: Jul. 4, 1989

[54] AUTOMATIC LANCET DEVICE

[75] Inventors: Daniel J. Chiodo; Joseph A. Maggio, both of Hialeah, Fla.

[73] Assignee: Medicore, Inc., Hialeah, Fla.

[21] Appl. No.: 132,602

[22] Filed: Dec. 14, 1987

[51] Int. Cl.⁴ .............................................. A61B 17/32
[52] U.S. Cl. ................................................ 128/314
[58] Field of Search ................... 128/314, 315, 329 R, 128/330; 604/22, 46, 47, 134–137, 156, 157

[56] References Cited

U.S. PATENT DOCUMENTS

| | | | |
|---|---|---|---|
| 3,760,809 | 9/1973 | Campbell, Jr. | 128/314 |
| 4,230,118 | 10/1980 | Holman et al. | 128/314 |
| 4,517,978 | 5/1985 | Levin et al. | 128/314 |
| 4,539,988 | 9/1985 | Shirley et al. | 128/314 |
| 4,580,565 | 4/1986 | Correll et al. | 128/314 |
| 4,658,821 | 4/1987 | Chiodo et al. | 128/314 |
| 4,715,374 | 12/1987 | Maggio | 128/314 |

Primary Examiner—Max Hindenburg
Attorney, Agent, or Firm—Oltman and Flynn

[57] ABSTRACT

A reusable automatic lancet device having a removable finger rest with an opening for passing the lancet needle to prick a patient's finger below the finger rest. A pivoted arm which holds the lancet needle is locked in a cocked position before the finger rest is inserted and it is released in response to upward pressure of the patient's finger against the finger rest after its insertion. The locking mechanism for the arm includes a pivoted pressure lever with upstanding segments at the back to engage the cocked arm and a slot open at the front to receive the finger rest, an ejector slidably mounted on the pressure lever and holding it locked against movement until the finger rest is inserted, an ejector lock bar slidably and pivotally mounted behind the ejector and having an upstanding segment at the back to engage the cocked arm, a pivoted ejector lock arm overlying the pressure lever and cooperating with the ejector, and a plastic spring biasing the ejector lock arm downward and providing a limit stop for the arm when it is released from its cocked position.

19 Claims, 5 Drawing Sheets

AUTOMATIC LANCET DEVICE

SUMMARY OF THE INVENTION

This invention relates to an automatic surgical lancet device.

Various automatic surgical lancets have been proposed which have a lancet needle on the free end of a pivoted arm which is moved by spring force from a retracted, cocked position to an operating position in which the needle pricks a person's finger to yield a blood sample. Typically, the arm is released from its cocked position by the pressure of a finger different from the finger that will be penetrated by the lancet needle.

U.S. patent application Ser. No. 06/930,515 filed Nov. 14, 1986, by one of the co-inventor herein, now U.S. Pat. No. 4,715 discloses a disposable, single-use lancet in which the cocked arm carrying a lancet needle assembly inside the housing is released by the force of a patient's finger that is to be pricked by the lancet needle.

The present invention is directed to a novel automatic lancet designed for repeated uses and having a novel arrangement for releasing the cocked arm, which carries a lancet needle assembly on the outside of the housing, in response to the force of the patient's finger that is to be pricked by the lancet needle.

Another object of this invention is to provide a reusable automatic lancet device having a novel arrangement for preventing an inadvertent release of the cocked arm which carries the lancet needle.

Preferably, the present automatic lancet device has a pivoted pressure lever inside its housing which is arranged to hold a lancet needle-carrying arm in a raised, cocked position as long as the lever is down. The lever is held down by a slidably displaceable ejector, which is prevented from releasing the lever by a pivoted ejector lock arm above and a slidable and pivoted ejector lock bar behind it. The ejector lock bar also holds the arm cocked. The ejector lock arm releases the ejector when an apertured finger rest for the patient's finger is inserted into a slot in the pressure lever from in front of the housing. This permits the ejector to be slid back, pushing the ejector lock bar back so that it releases the cocked arm. When the patient's finger presses up against the finger rest in front of the housing, this pivots the pressure lever in a direction to release the cocked arm. The arm moves down quickly from its cocked position and the lancet needle penetrates the patient's finger which is pushing up on the finger rest. Afterwards, the finger rest may be removed by sliding the ejector forward.

Further objects and advantages of this invention will be apparent from the following detailed description of a presently-preferred embodiment shown in the accompanying drawings.

Before explaining the disclosed embodiment of the present invention in detail it is to be understood that the invention is not limited in its application to the details of the particular arrangement shown since the invention is capable of other embodiments. Also, the terminology used herein is for the purpose of description and not of limitation.

DETAILED DESCRIPTION

In broad outline, the embodiment of the invention shown in the drawings has a housing 10 (FIG. 1), an ejector 20 (FIG. 3) slidably mounted on the bottom of the housing, a pressure lever 30 pivotally mounted in the housing above the ejector (FIG. 4) and having its front end projecting outside the housing, an ejector lock arm 70 is slidably and pivotally mounted in the housing on the same pivot as pressure lever 30, an ejector lock arm 95 pivotally mounted on the pressure lever, a plastic spring 110 which biases the ejector lock arm 95 down against the pressure lever, a lancet holder arm 120 pivotally mounted in the housing and carrying a holder 138 for a lancet needle assembly on its free end in front of the housing, a spring 127 for moving the arm down, and a finger rest 145 (FIG. 5) which is slidably insertable into and removable from the pressure lever 30 at the front of the housing.

Figures 1, 2, 3:
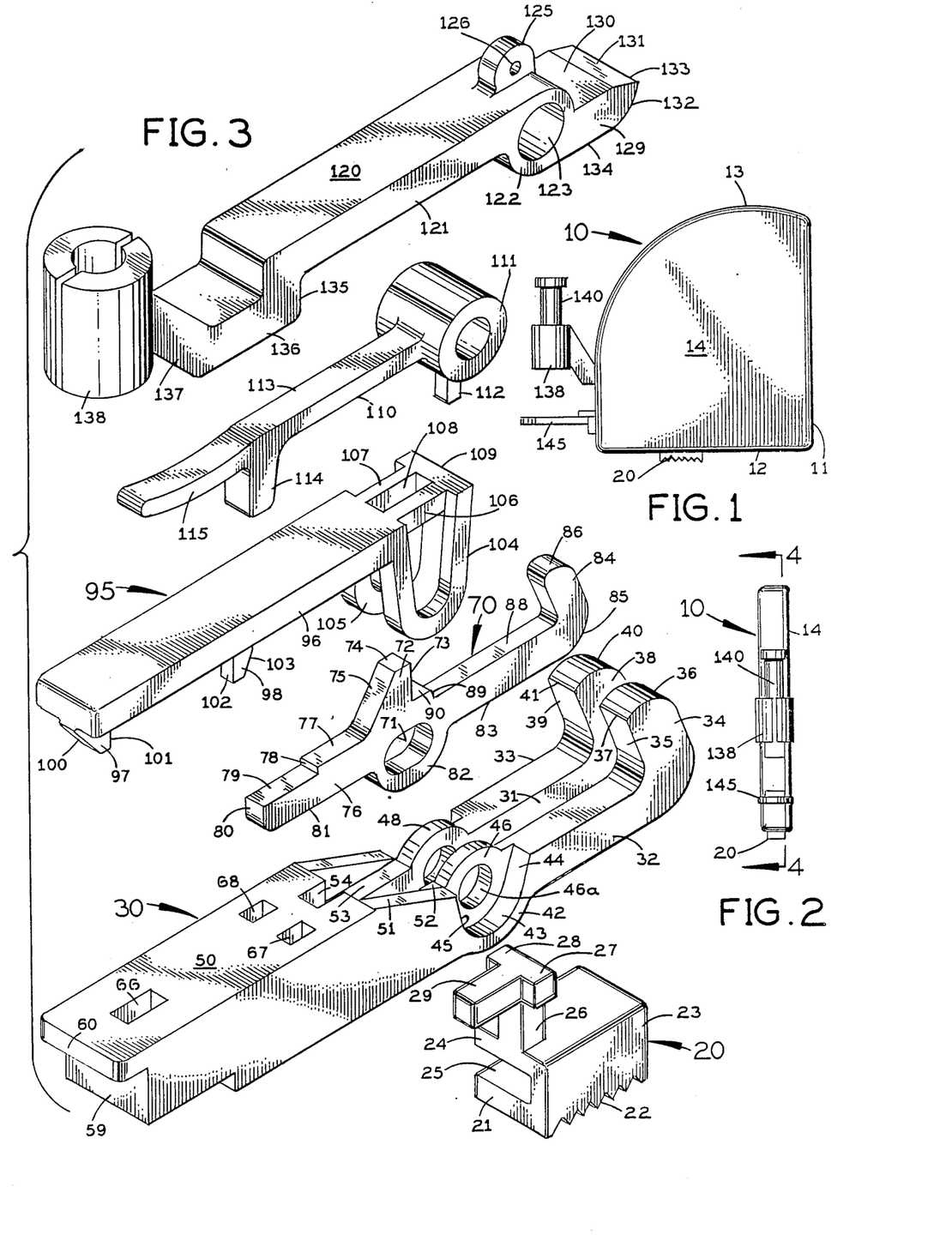
FIG. 1 is a side elevation of the present automatic lancet device.
FIG. 2 is a front elevation taken from the left side of FIG. 1.
FIG. 3 is an exploded perspective view showing most of the moving parts in the lancet device.
Figure 4:
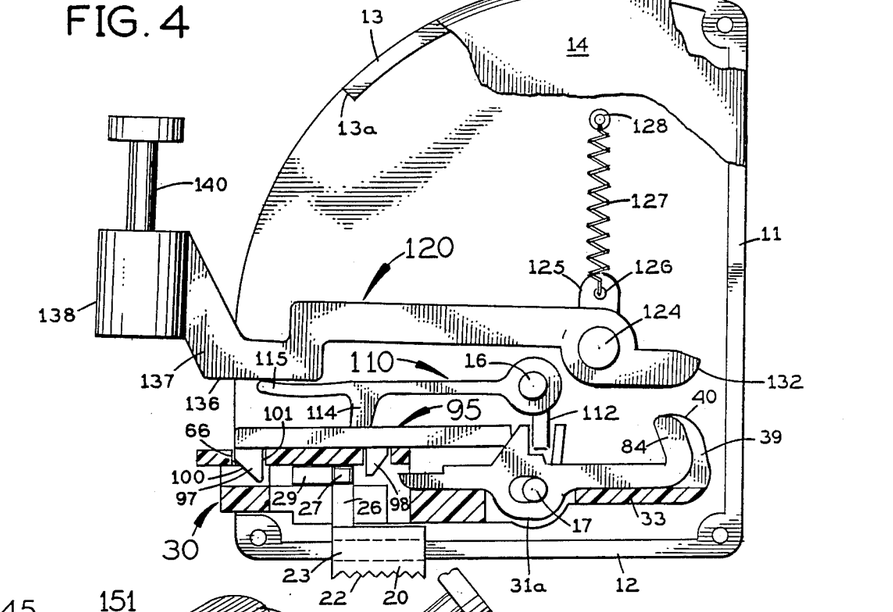
FIG. 4 is a longitudinal section showing the positions of the parts before the lancet device is used.
Figures 7, 8, 9:
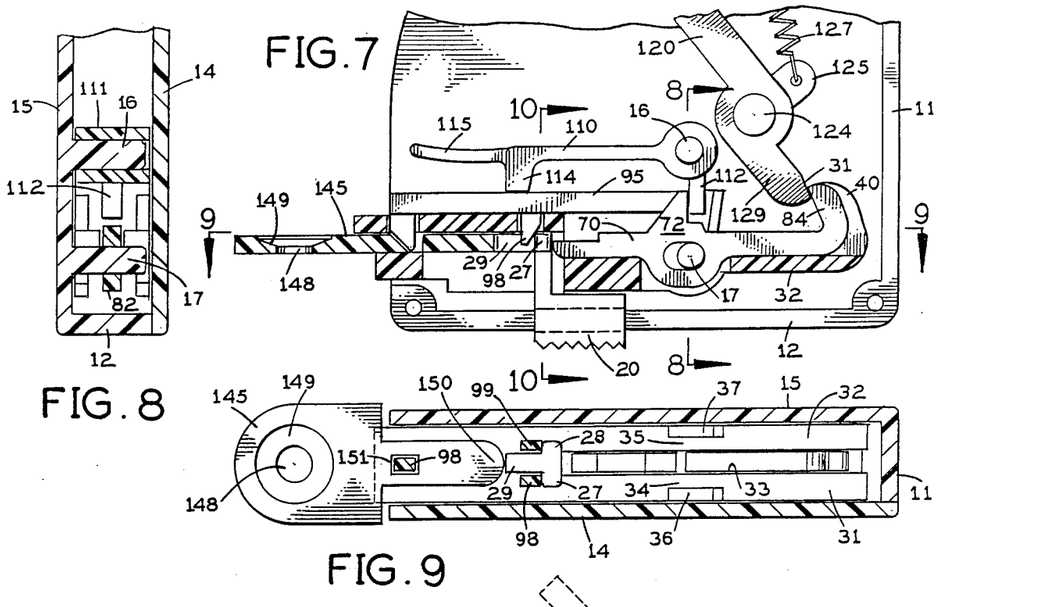
FIG. 7 is a similar view showing the finger rest fully inserted.
FIG. 8 is a fragmentary vertical cross-section taken along the line 8—8 in FIG. 7.
FIG. 9 is a longitudinal section taken along the horizontal line 9—9 in FIG. 7.

Referring to FIG. 1, the housing 10 of the lancet has a flat vertical back wall 11, a flat horizontal bottom wall 12 extending perpendicular to the back wall, and a convex wall 13 at the top which, as shown in FIG. 4, extends forward and then downward from the upper end of the back wall. Housing 10 has flat opposite side walls 14 and 15 (FIGS. 8 and 9) and it is open at the front below the lower edge 13a (FIG. 4) of its convex top wall 13. As shown in FIG. 9, the back wall 11 is molded integral with side wall 15, and this is also true of the bottom wall 12 and the top wall 13. Side wall 14 is a separately molded piece which is attached to the other piece 11-12-13-15 of the housing by screws. Approximately the front half of the bottom wall 12 is recessed immediately behind side wall 14 to provide a narrow slot 12a (FIG. 10) which extends from the bottom front corner of the housing back along the bottom wall. As shown in FIG. 8, a cylindrical upper pin 16 and a cylindrical lower pin 17 extend inward from the housing side wall 15 and terminate a short distance from the opposite side wall 14. These pins are aligned vertically, as shown in FIG. 7.

Figures 10, 11:
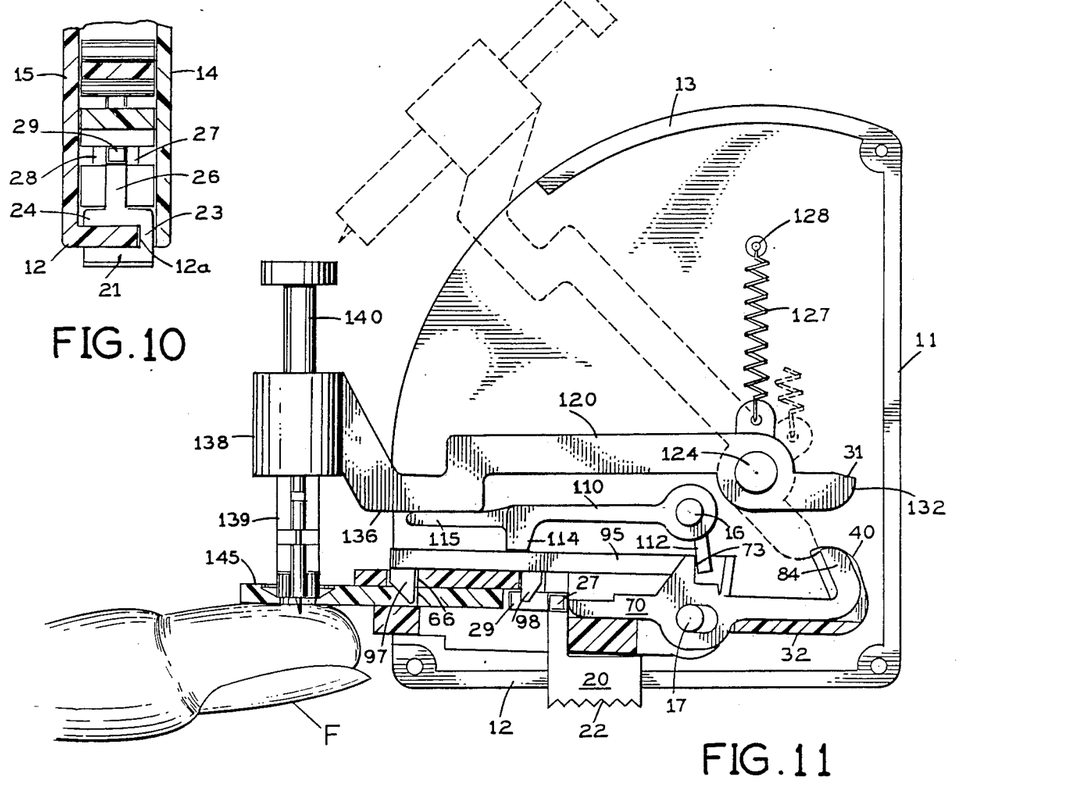
FIG. 10 is a vertical cross-section taken along the line 10—10 in FIG. 7.
FIG. 11 is a view like FIGS. 6 and 7, showing the needle-carrying arm moved down from its cocked position (shown in phantom) to its operating position in which the needle penetrates a patient's finger.
Figure 12:
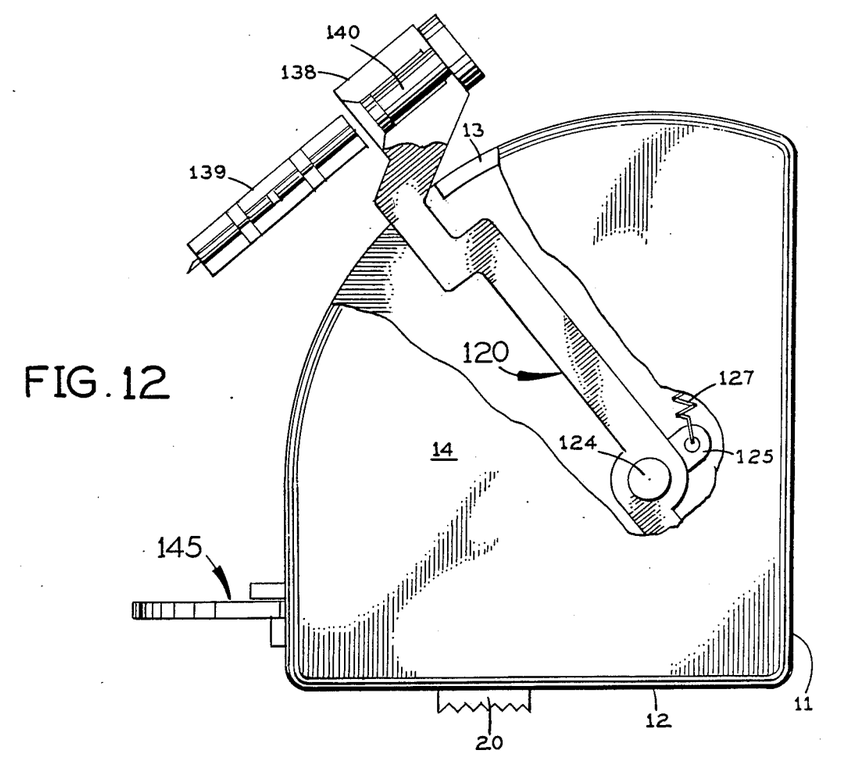
FIG. 12 is a side elevation, with part of the housing of the device broken away, showing the needle-carrying arm raised to its cocked position.

As best seen in FIG. 3, the ejector 20 has a flat bottom segment 21 with a serrated outside face 22, a short vertical side segment 23 which extends up from the bottom segment 21 at the side of the ejector closest to the housing side wall 14, and a flat intermediated segment 24 which extends in from the top of side segment 23 parallel to the bottom segment 21 to form a recess 25 of rectangular cross-section which extends the full length of the ejector and is open at its opposite ends. Thus, the segments 21, 23 and 24 of the ejector form a channel which is slidable along the bottom wall 12 of the housing where it has the slot 12a. As shown in FIG. 10, the side segment 23 of the ejector is slidably received in slot 12a, with the intermediate segment 24 of the ejector slidably engaging the housing bottom wall 12 from above and the bottom segment 21 of the ejector closely below the housing bottom wall.

Referring again to FIG. 3, the ejector 20 has a vertical post segment 26 of rectangular cross-section extending up from the intermediate wall 24 at its front end. At the top of this post segment 26 is a generally T-shaped top element having a pair of rectangular legs 27 and 28 extending out on opposite sides of post segment 26 (toward the respective side walls 14 and 15 of housing 10, as shown in FIG. 10) and a front segment 29 of rectangular cross-section extending forward beyond the front edge of the ejector at its segments 26,24,23 and 21.

Toward its back end (the right end in FIG. 3), the horizontally elongated pressure lever 30 has a longitudinal slot 31 which is open at the top and closed at the bottom. This slot separates opposite longitudinal legs 32 and 33 along the top of the pressure lever. These legs are joined integrally along the bottom of the pressure lever. A transverse end segment 34 extends up from leg 32 at its back end in FIG. 3, presenting a flat front face 35 which extends upward and forward at a 70 degree angle to the longitudinal axis of the pressure lever and a convex outer face 36 at the top which forms a sharp corner at 37 with the flat front face 35. The other 33 has an identical transverse end segment 38 with a flat front face 39 and a convex outer face 40 at the top which intersects the inside face at a sharp corner 41.

About midway along the pressure lever 30 on the outside of the lever its longitudinal leg 32 is joined to a generally U-shaped segment 42 which defines an open-topped recess having a round bottom surface 43 between upwardly diverging, opposite, flat, rear and front side faces 44 and 45. Between this recess and the longitudinal slot 31 the pressure lever presents a rounded ear 46 having a circular opening 46a for receiving the lower pivot pin 17 on the housing. The longitudinal slot 31 is open at the bottom, as well as at the top, at the location of the U-shaped segment 42 and ear 46 and a short distance in front of and behind these elements lengthwise of the pressure lever, as shown at 31a in FIGS. 14 and 18.

The opposite side of pressure lever 40, where the longitudinal leg 33 is located, has an identical generally U-shaped segment extending from leg 33 and defining a recess 47 on the outside of the lever, and a rounded ear 48 next to the longitudinal slot 31 in the lever. Ear 48 has a circular opening 48a coaxial with the opening 46a in the ear 46 on the opposite side of slot 31 for receiving the lower pivot pin 17.

Figure 14:
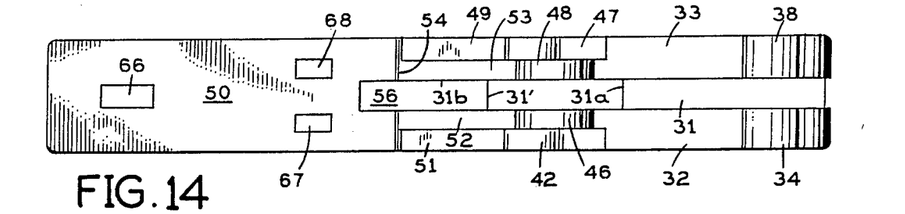
FIG. 14 is a top plan view of the pressure lever in this lancet device.
Figure 15:
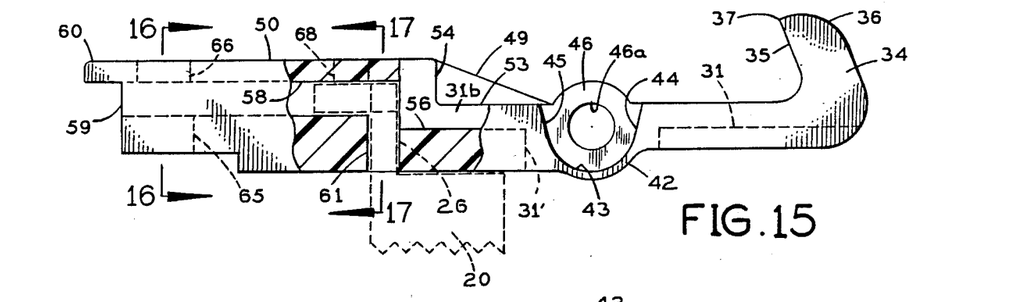
FIG. 15 is a slide elevation of this pressure lever, with part of it in section, and with the finger rest ejector in phantom.

Beginning a short distance in front of the pivot ears 46 and 48 (to the left in FIG. 3), the longitudinal slot in pressure lever is open at the top and closed at the bottom, as shown at 31b in FIGS. 14 and 15. The pressure lever presents an internal, vertical, rearwardly-facing shoulder 31' at the intersection of its slot segments 31a and 31b. An inclined top surface 49 in front of recess 47 in FIGS. 3,15 and 19 extends forward and upward at a slight angle to a horizontal top surface 50 which extends forward the remaining length of the pressure lever. An identical inclined surface 51 extends up from the recess defined by the generally U-shaped segment 42 on the opposite side of the pressure lever. Next to the longitudinal slot segment 31b and laterally inward from the inclined surfaces 51 and 49, the pressure lever presents horizontal top faces 52 and 53 extending forward from the respective ears 46 and 48 at the same level as the top faces of legs 32 and 33 on the back side of the pivot ears 46 and 48. As shown in FIG. 3, the top face 53 ends at a vertical face 54, which extends up to the back edge of top surface 50. A similar vertical face 55 (FIG. 14) extends from the front end of top face 52 up to top face 50 on the opposite side of the longitudinal slot in pressure lever 30.

Figures 16, 17, 18, 19:
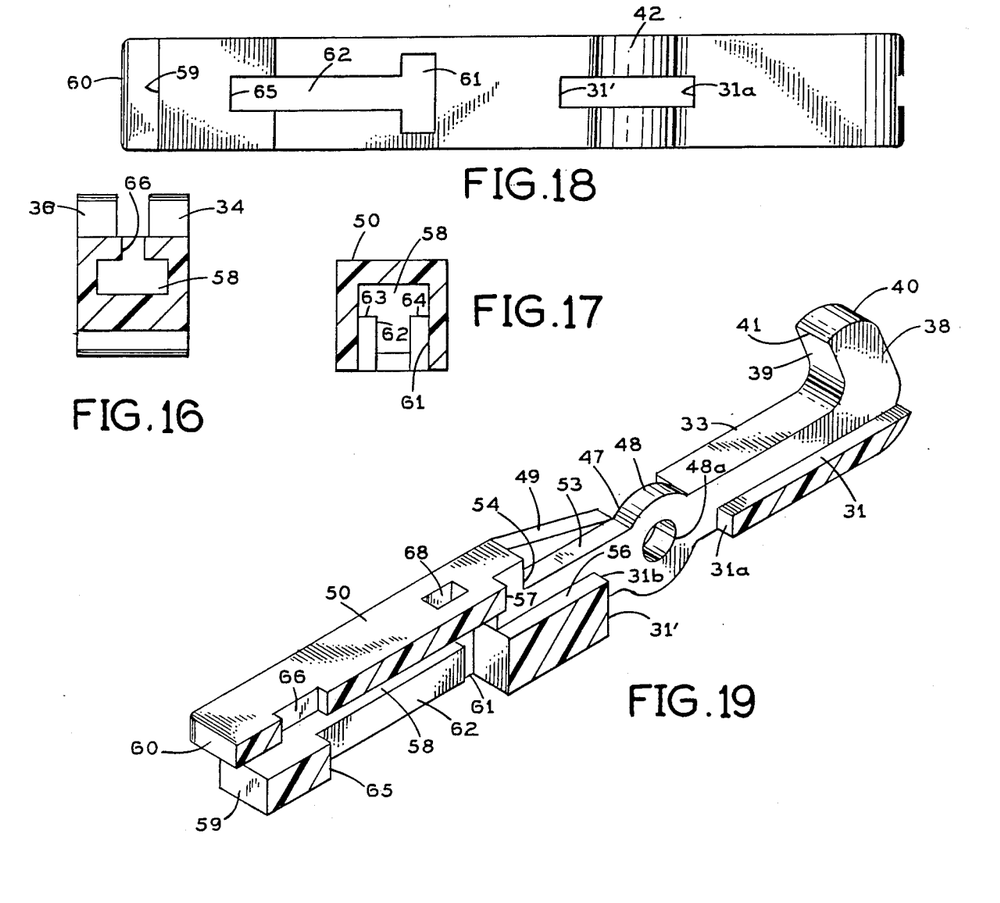
FIG. 16 is a vertical cross-section taken along the line 16—16 in FIG. 15.
FIG. 17 is a similar view taken along the line 17—17 in FIG. 15.
FIG. 18 is a bottom plan view of the pressure lever.
FIG. 19 is a perspective view of the pressure lever with parts broken away for clarity.

The longitudinal slot segment 31b in front of the pivot ears 46 and 48 has a horizontal bottom face 56 (FIGS. 15 and 19) at the same level as the coaxial centers of the pivot pin openings 46a and 48a in these ears. Slot segment 31b extends forward beyond the vertical faces 54 and 55 to the back end of a horizontal slot 58 of rectangular cross-section (FIG. 17). Slot 58 is offset upwardly from the bottom face of slot segment 31b, as shown in FIG. 15. Slot 58 extends forward through the front part of the pressure lever to a vertical front face 59 of the pressure lever (FIG. 3) below a forwardly projecting extension or lip 60 on the front end of the pressure lever.

Directly below slot 58 the pressure lever 30 has a slot of generally T-shaped configuration (FIG. 18), with the cross arm 61 at the back end of the T extending the full width of slot 58 at its back end and the longitudinal arm 62 of the T extending forward from the cross arm 61 centrally below slot 58 for substantially less than the full width of slot 58. The T-slot 61,62 is open its entire extent along the bottom of the pressure lever, and at the top it opens into the slot 58 above. At its intersection with the narrower longitudinal arm 62 of the T-slot (FIG. 17), the slot 58 provides a pair of upwardly-facing horizontal surfaces 63 and 64 on opposite sides of the T slot. The front end of the longitudinal arm 62 of the T slot is at a vertical internal face 65 (FIGS. 15, 18 and 19) spaced behind the front face 59 of the pressure lever.

A short distance in front of this face 65, the pressure lever has a front top opening 66 (FIGS. 3 and 15) of elongated rectangular shape which extends down into the slot 58, as shown in FIG. 16.

The pressure lever has two rear top openings 67 and 68 of rectangular shape which extend down into slot 58 immediately in front of the cross arm 61 of the T slot in the bottom of the pressure lever.

FIG. 15 shows in phantom the ejector 20 in the position on the pressure lever 30 in which it permits pivotal movement of the ejector lever on the lower pivot pin 17. In this position of the parts, the post segment 26 of the ejector is centered in the cross arm 61 of the T slot 61,62 in the bottom of the pressure lever, the lugs 27 and 28 on the top of the ejector are slidably received in slot 58 above the cross arm 61 of the T slot, and the front segment 29 at the top of the ejector is received centrally in slot 58 directly above the narrower longitudinal arm 62 of the T slot. The front top segment 29 of the ejector is slightly narrower than the longitudinal arm 62 of the T slot, permitting pressure lever 30 to pivot upward in front of its pivot pin 17.

When the ejector 20 is displaced forward from the position shown in FIGS. 14–16 its top lugs 27 and 28 slide across the bottom surfaces 64 and 63 of slot 58 on opposite sides of the narrower longitudinal arm of T-slot 61,62, so now the pressure lever cannot move pivotally because the ejector 20 (which is coupled at its slot 25 to the bottom wall 12 of the housing, as shown in FIG. 10) prevents it.

Referring to FIG. 3, the ejector lock bar 70 has an oblong, horizontally elongated, rounded opening 71 which slidably passes the lower pivot pin. The vertical dimension of this opening is substantially equal to the diameter of each pivot ear opening 46a and 48a in pressure lever 30. The horizontal dimension of opening 71 in the ejector lock bar is substantially greater than the diameter of opening 46a and 48a in the pressure lever, so that the ejector lock bar can be slid horizontally back and forth across the lower pivot pin 17.

At the top, the ejector lock bar 70 presents an upwardly extending projection 72 having a vertical rear face 73 aligned with the center of its opening 71, a short horizontal top face 74 extending forward from the rear face 73, and a forwardly and downwardly inclined, flat front face 75.

In front of the projection 72 the ejector lock bar has a horizontally elongated front leg 76 with a flat horizontal top face 77 extending forward from the inclined face 75, and a short vertical surface 78 extending down from the front end of face 77 to a forwardly extending horizontal top face 79. A convex front surface 80 of the ejector lock bar curve downward and rearward from the front edge of top face 79 and merges smoothly with a flat elongated bottom face 81, which lies in the same horizontal plane as the center of opening 71.

Below the opening 71, the ejector lock bar presents a convex oblong segment 82.

In back of the opening 71, the ejector lock bar has an elongated, horizontal bottom face 83 which is coplanar with its bottom face 81 in front of the opening. At its back end the ejector lock bar presents an upwardly extending, forwardly inclined projection 84 which forms a convex bottom rear corner 85 with the bottom surface 83. Projection 84 presents a convex top surface 86 which extends forward to a downwardly and rearwardly inclined, flat front face 87 lying in a plane at 70 degrees to the longitudinal axis of the ejector lock bar.

In front of its rear projection 84 the ejector lock bar presents an elongated, flat top face 88 lying in the same horizontal plane as the top face 77 in front of opening 71. Face 88 extends forward along the ejector lock bar to a rounded rearwardly-facing shoulder 89 which joins it to a short horizontal top face 90 extending forward to the lower end of vertical face 73.

The ejector lock bar 70 fits snugly but slidably in the longitudinal slot 31 in pressure lever 30, with the back end projection 84 of the ejector lock bar between the back end segments 34 and 38 of the pressure lever, the bottom face 83 on the back part of the ejector lock bar resting on the bottom of slot 31 in the pressure lever behind the lower pivot pin 17, as shown in FIG. 4, the bottom face 81 on the front part of the ejector lock bar resting on the bottom face 56 of slot segment 31b in the pressure lever in front of pivot pin 17, the oblong opening 71 in the ejector lock bar registering with the pivot ear openings 46a and 48a in the pressure lever, and the projection 72 on top of the ejector lock bar above its opening 71 extending up above the top of the pivot ears 46 and 48 on the pressure lever.

The ejector lock bar 70 is slidable across the lower pivot pin 17 lengthwise of the pressure lever 30 between a forward position (FIGS. 4,6 and 7) and a rearward position (FIG. 11). In its forward position the rounded front end 80 of the ejector lock bar extends in to the back end of slot 58 in the pressure lever directly above cross arm of the T-slot 61,62 in the bottom of the pressure lever. In its rearward position the front end of the ejector lock bar is behind the slot 58 in the pressure lever.

The ejector lock arm 95 (FIG. 3) has a horizontally elongated front segment 96 of rectangular cross-section with a depending lug 97 at its front end, which is receivable in the front top opening 66 in pressure lever 30, and a pair of laterally spaced, depending rear lugs 98 and 99 (FIG. 9), which are receivable in the rear top openings 67 and 68 in the pressure lever. The front lug 97 has a rearwardly and downwardly inclined front face 100 and a vertical back face 101. The rear lug 98 has a vertical front face 102 and a rearwardly and upwardly inclined back face 103. The other rear lug 99 is identical to lug 98.

At its back end the ejector lock arm 95 presents a pair of laterally spaced downwardly extending, generally U-shaped segments 104 and 105. Laterally inward from these U-segments the ejector lock arm presents longitudinal, straight, top segments 106 and 107, which are continuations of its front segment 96. The ejector lock arm is open at 108 between the straight segments 106 and 107. At the extreme back end of the ejector lock arm, its U-segments 106 and 107 are connected at the top be a cross-piece 109.

The bottom curvature of the U-segments 104 and 105 of ejector lock arm 95 is approximately complementary to the recesses in pressure lever 30 outside its pivot ears 46 and 48 such that the two parts fit snugly together but each can pivot a limited angular amount with respect to the other about the axis of the lower pivot pin 17.

The top opening 108 at the back end of the ejector lock arm 95 receives the projection 72 on the top of the ejector lock bar 70, as shown in FIG. 4.

The plastic spring 110 has a ring 111 on its back end which receives the upper pin 16 on the inside of the housing with a tight fit to mount the spring on this pin. A rear lug 112 extends down from ring 111 into the top rear opening 108 in ejector lock arm 95 behind the top projection 72 on ejector lock arm 70, as shown in FIG. 4.

The plastic spring 110 presents an elongated flexible and resilient front arm 113 extending horizontally in front of its rear ring 111. A front lug 114 extends down from arm 113 and engages the top of the front segment 96 of ejector lock arm 95, as shown in FIG. 4. In front of this lug the plastic spring presents a slightly curved extension 115 of its arm 113. Extension 115 is concave on the top and convex on the bottom As shown in FIG. 4, the spacing between the vertical back face 101 of the depending front lug 97 on ejector lock arm 95 and the vertical front face 102 of its rear lug 98 and the coplanar front face of its other front lug 99 is greater than the length of ejector 20 along the top 27,28 and 29. Therefore, when the ejector lock arm 95 is down, the ejector 20 can be positioned anywhere between the stops provided by these lugs on the bottom of the ejector lock arm. Throughout this limited range of positions of ejector 20 from front to back on the housing, its top lugs 27 and 28 overlie the internal upwardly facing surfaces 63 and 64 (FIG. 17) of the pressure lever 30 at the bottom of its slot 58. Thus, throughout this limited range of positions of ejector 20, which can be called its "normal position", it locks the pressure lever 30 against pivotal movement.

The lancet holder arm 120 an elongated straight segment 121 extending forward from a generally cylindrical segment 122, which defines a cylindrical opening 123 for slidably receiving a rear pivot pin 124 (FIG. 4) located inside the housing behind and above the upper pin 16 on which spring 110 is mounted. A vertical ear 125 projects up from the cylindrical segment 122 of the lancet holder arm and presents an opening 126 for anchoring the lower end of a coil spring 127 (FIG. 4) whose upper end is fastened to the inside of the housing at 128. Spring 127 is under tension.

Behind its cylindrical segment 122 the lancet holder arm has a rear segment 129 with a flat top face 130 in the same horizontal plane as the axis of the opening 123, a tapered top rear face 131 which is inclined downward and rearward from the back edge of top face 130, a convex bottom rear face 132 which curves downward and forward from a sharp corner 133 with face 131, and a flat bottom face 134 extending forward from the curved face 132 and merging smoothly with the bottom of cylindrical segment 122.

Referring to FIGS. 4 and 7, the position and curvature of the convex bottom rear face 132 of lancet holder arm 120 are such that it slides across the curved top rear faces 36 and 40 of pressure lever 30 and the curved top rear face 86 of ejector lock bar 70 when the lancet holder arm is raised from its normal, substantially horizontal position in which spring 127 extends vertically and has its shortest length (FIG. 4) to a cocked position (FIG. 7) is which it is raised clockwise to a position in which spring 127 is at an angle to the vertical and is stretched more. In this cocked position, the tapered top rear face 131 of lancet retainer arm 120 engages the inclined faces 35 and 39 of pressure lever 30 and the similarly inclined face 87 of ejector lock bar 70.

At the front end of its elongated segment 121 the lancet holder arm 120 presents in succession a short, downwardly extending vertical segment 135, a downwardly offset, forwardly extending, horizontal, bottom segment 136, and an upwardly and forwardly inclined segment 137 joined to a holder 138 for a lancet needle assembly. When the lancet holder arm 120 is in its normal lowered position (FIG. 4) its downwardly offset bottom segment 136 rests on top of the front end extension 115 of the plastic spring 110.

Preferably, the holder 138 is constructed substantially as described in U.S. Pat. No. 4,658,621 to Daniel J. Chiodo, et al for receiving a lancet needle assembly, shown at 139 in FIG. 6, and a plunger 140 for pushing the lancet needle assembly out of holder 138 after use.

The finger rest 145 (FIG. 5) is a generally flat body having a wide front segment 146 and a narrow rear segment 147 extending behind the front segment.

Figures 5, 6:
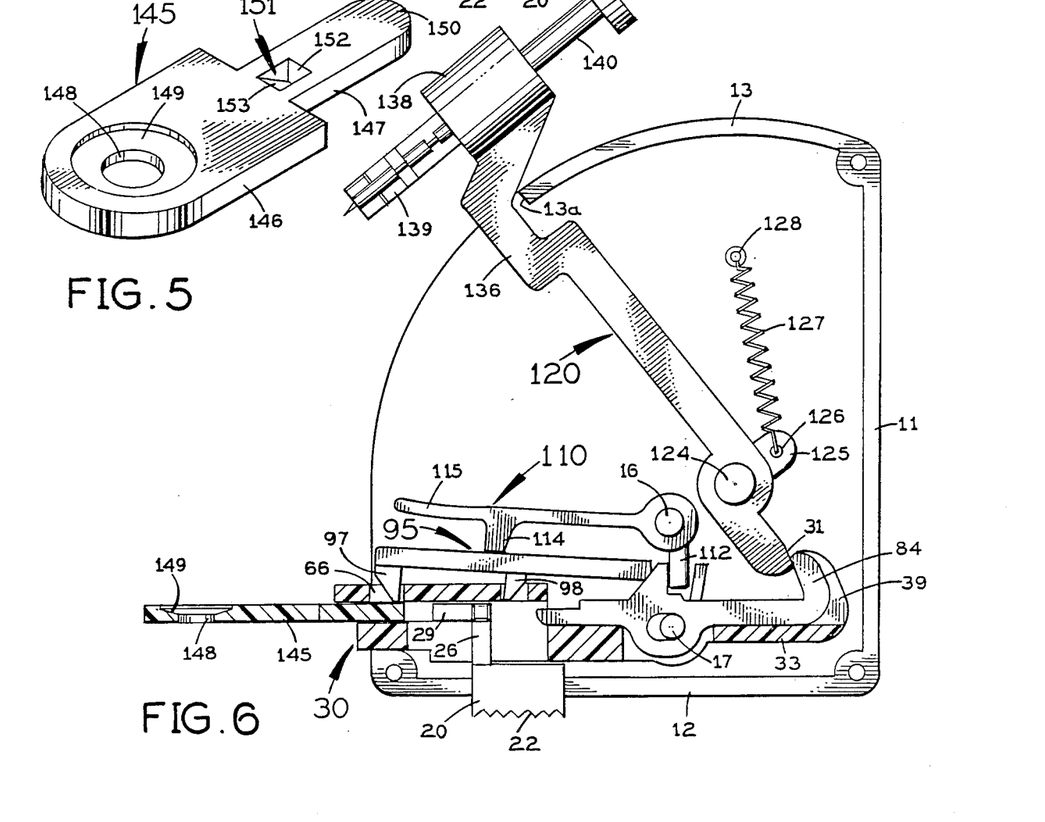
FIG. 5 is a perspective view of a manually insertable and removable finger rest for the lancet device.
FIG. 6 is view like FIG. 4, showing the positions of the parts when the finger rest is partially but not fully inserted.

The front segment is formed with a circular opening 148 for passing the lancet needle when the lancet holder arm 120 moves down from the cocked position shown in phantom in FIG. 11 to the operative position shown in full lines in that Figure. As best seen in FIG. 6, finger rest 145 presents a frustoconical, flared surface 149 surrounding the opening 148 at the top. When the lancet retainer arm 120 moves down from its cocked position, the lancet needle assembly strikes this flared surface 149 on finger rest 145 to limit the lancet needle's penetration into the patient's finger, as shown in full lines in FIG. 11.

The rear segment 147 of the finger rest has a semicircular, convex back face 150. The width of the rear segment is such that it can be slidably inserted from the front into the slot 58 is pressure lever 30. When it enters this slot (FIG. 6), its rounded back face 150 engages the tapered front face 100 of the depending front lug 97 on ejector lock arm 95 to raise the ejector lock arm pivotally.

A short distance behind its juncture with the front segment 146, the rear segment 147 of the finger rest presents an opening 151 having a vertical rear face 152 and a downwardly and rearwardly inclined front face 153 with a slope that substantially matches that of the tapered front face 100 of lug 97 on ejector lock arm 95. As shown in FIG. 7, the front depending lug 97 on ejector lock arm 95 drops into this opening 151 in the finger rest after it has been fully inserted.

OPERATION

FIG. 4 shows the normal position of the parts of the lancet device, with the lancet holder arm 120 down and the finger rest 145 not yet inserted. The spring 127 is vertical, the opening 126 in the ear 125 on top of the lancet holder arm 120 being vertically aligned with the fastening point 128 for the upper end of the spring. The ejector 20 is positioned forward along the pressure lever 30, and the cross lugs 27 and 28 on the top of the ejector overlie the upwardly facing surfaces 63 and 64 (FIG. 17) at the bottom of slot 58 on opposite sides of the narrower longitudinal segment 62 of the T-slot 61,62 in the bottom of pressure lever 30. The recess 25 in ejector 20 receives the bottom wall 12 of the housing so that the ejector is held against movement up or down in the housing. In turn, the ejector prevents pivotal movement of pressure lever 30 as long as the ejector is in this forward position.

In this position of the parts, the weight of the lancet holder arm 120 bears down on the plastic spring 110, which holds the ejector lock arm 95 down, with its depending lugs 97,98 and 99 received in the corresponding top openings 66,67 and 68 in pressure lever 30. The rear lugs 98 and 99 project down far enough into slot 58 in pressure lever 30 to block the top of ejector 30 behind its cross lugs 27 and 28, so the user cannot retract the ejector past these lugs 98 and 99 on ejector lock arm 95. The ejector 20 has a limited "play" from front to back along the housing between front lug 97 and rear lugs 98 and 99 on ejector lock arm 95 without changing the condition of any of the other parts. The ejector lock bar 70 is in its forward position on pressure lever 30, with the back edge of its oblong opening 71 engaging the lower pivot pin 17 on the inside of the housing.

The finger rest 145 may be inserted before or after the lancet holder arm 120 is raised clockwise from its FIG. 4 position to the cocked position shown in FIG. 6.

When the finger rest 145 is pushed into slot 58 in pressure lever 30, its back edge raises the depending front lug 97 of ejector lock arm 95, pivoting this lock arm clockwise, as shown in FIG. 6, and raising its depending rear lugs 88 and 89 far enough to permit the user to use light finger pressure to manually retract the ejector 20 against the front edge of the ejector lock bar 70. The plastic spring 110 flexes upward to permit such pivotal movement of the ejector lock arm. The ejector lock bar 70 remains in its forward position to which it is biased by plastic spring 110, whose depending rear lug 112 engages the vertical back face 73 of the top projection 72 on the ejector lock bar. This position of the ejector 20 is a partially retracted position.

The user continues to push the finger rest 145 in until it reaches the position shown in FIG. 7. Here, the front depending lug 97 on ejector lock arm 95 has dropped into the opening 151 in finger rest 145 to lock it in its fully inserted position. The depending rear lugs 98 and 99 on ejector lock arm 95 have dropped in front of the cross lugs 27 and 28 on ejector 20 at the top.

When the user raises the lancet holder arm 120 (either before or after inserting finger rest 145), the convex surface 132 on the bottom of its rear segment 129 rides forward across the convex top surfaces 36 and 40 on the upstanding rear segments 34 and 38 of pressure lever 30 and across the covex top surface 86 of the upstanding rear segment 84 of ejector lock bar until the inclined face 131 of the lancet holder arm engages the inclined front faces 35,39 and 87 of the pressure lever and the ejector lock bar. This pivotal movement of the lancet holder arm 120 lengthens, and therefore increases the tension of, its spring 127. The upstanding rear segments 34 and 38 of pressure lever 30 and the upstanding rear segment 84 of ejector lock bar 70 lock the lancet holder arm 120 in its cocked position. To release the lancet holder arm from its cocked position, so that spring 127 can move it down forcefully, the ejector lock bar 70 must be moved back and the pressure lever 30 must be pivoted clockwise in FIG. 7.

The ejector lock bar 70 is moved back by sliding the ejector 20 back from the partially retracted position shown in FIG. 7 to the fully retracted position shown in FIG. 11, in which the vertical segment 26 of the ejector abuts against the pressure lever 30 at the back of the cross arm 61 or the T-slot 61,62 in the bottom of the pressure lever. When slid back this way, the ejector 20 pushes the ejector lock bar 70 back (as permitted by its oblong opening 71 for pivot pin 17), thereby disengaging the upstanding rear segment 84 of the ejector lock bar 70 from the rear segment 129 of lancet holder arm 120. The ejector 20 now is positioned with its cross lugs 27 and 28 at the top completely behind the shoulders 63 and 64 on the bottom of slot 58 in the pressure lever 30. Consequently, the pressure lever 30 can pivot on the lower pivot pin 17.

Such pivotal movement of the pressure lever occurs when the patient's finger F (FIG. 11) is pushed up against the bottom of finger rest 145. The upward force exerted by the patient's finger against finger rest 145 is exerted against the pivoted pressure lever 30 because of the close engagement of the rear segment 147 of the finger rest in slot 58 in the pressure lever. Pressure lever 30 pivots counterclockwise to the position shown in FIG. 11. This lowers the back end of the pressure lever, moving its upstanding segments 34 and 38 down past the rear segment 129 of lancet holder arm 120. The tension spring 127 now pulls the released lancet holder arm 120 down from its cocked position and the lancet needle it carries pierces the patient's finger F, as shown in FIG. 11. The curved front end segment 115 of plastic spring 110 cushions the impact of the lancet holder arm at the end of its downward travel and prevents the spring 127 from moving over-center at the end of the downward movement of the free end of the lancet holder arm 120. That is, the lower end of spring 127 never moves forward past its upper end (i.e., to the left in the drawings).

Figure 13:
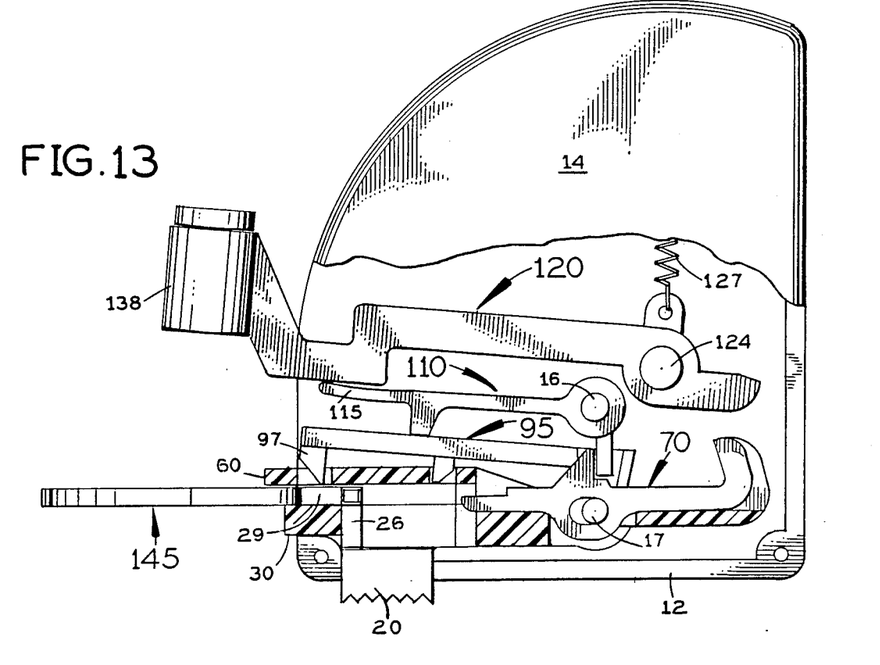
FIG. 13 is a similar view showing the finger pad being ejected after the lancet device has operated.

The finger rest 145 may be removed from pressure lever 30 by manually sliding the ejector 20 forward, as shown in FIG. 13. This is the forwardmost position of the ejector, in which its vertical segment 26 engages the internal vertical face 65 at the front end of the T-slot 61,62 on the bottom of the pressure lever. The transverse lugs 27 and 28 on the top of the ejector engage the inclined rear faces of the depending lugs 98 and 99 on ejector lock arm 95, causing it to pivot upward and lift its depending front lug 97 out of the opening 151 in the finger rest. This forward movement of the ejector 20 pushes the finger rest out of slot 58 in pressure lever 30.

From the foregoing description and the drawings, it will be understood that the ejector 20 has four different positions along the housing:

(1) the normal position (FIG. 4) in which its T-shaped top 27–29 is somewhere between the depending front lug 97 and the depending rear lugs 98 and 99 on ejector lock arm 95;

(2) the partly retracted position (FIGS. 6 and 7) engaging the front end of ejector lock bar 70 when the ejector lock bar is in its forward position;

(3) the fully retracted position (FIG. 11) in which it has pushed ejector lock bar 70 back to its rear position;

and (4) the forwardmost position (FIG. 13) to which it is moved to push the finger pad 145 out of the pressure lever 30. From the foregoing it will be evident that:

(1) the functions of the pressure lever 30 are to hold the lancet holder arm 120 cocked, to receive and hold the finger rest 145 when it is inserted, and to release the cocked arm in response to upward pressure of a patient's finger on the finger rest 145;

(2) the functions of the finger rest 145 are to release the ejector 20 so that it can unlock the pressure lever 30, and thereafter to move the pressure lever to release the cocked lancet holder arm 120;

(3) the functions of the ejector 20 are to hold the pressure lever 30 locked against movement for releasing the cocked lancet holder arm 120 until after the finger rest 145 is fully inserted in the pressure lever, to push the ejector lock bar 70 back so that it releases the cocked lancet holder arm, and to eject the finger rest 145 after the lancet device has operated;

(4) the functions of the ejector lock bar 70 are to hold the lancet holder arm 120 cocked, to urge the ejector 20 to a position locking the pressure lever 30 against movement, and to release the cocked lancet holder arm 120 when the ejector 20 is slid back;

(5) the functions of the ejector lock arm 95 are to urge the pressure lever 30 down to a position holding the lancet holder arm 120 cocked before the finger rest 145 is inserted, to hold the ejector 20 positioned to lock the pressure lever in this down position before the finger rest is inserted, to release the ejector 20 when the finger rest is inserted part-way into the pressure lever 30, to lock the finger rest 145 in the pressure lever after it has been fully inserted therein, and to release the finger rest for ejection from the pressure lever when the ejector 20 is moved forward after an operation of the lancet device;

and (6) the functions of the plastic spring 110 are to bias the ejector lock arm 95 down against the pressure lever 30, to limit the movement of the lancet holder arm 120 when it is released from its cocked position, and to bias the ejector lock bar 70 forward to urge the ejector 20 to a position locking the pressure lever 30 against movement.

We claim:

1. A lancet device comprising:

a housing;

an arm mounted in the housing for movement between a retracted position and an operating position, said arm having an end outside said housing;

a holder on said end of the arm, said holder having means for holding a lancet needle assembly with a needle for piercing a patient's finger;

spring means urging said arm from said retracted position to said operating position;

a finger rest;

positioning means inside said housing for holding said finger rest positioned on the outside of said housing in the path of said holder when said arm moves from said retracted position to said operating position, said positioning means being operable to permit movement of said finger rest with respect to said housing in response to the pressure of a patient's finger against the finger rest;

and latch means in said housing for holding said arm in said retracted position against the urging of said spring means, said latch means being operable to release said arm from said retracted position in response to said movement of the finger rest.

2. A lancet device according to claim 1 and having a pivoted lever which has both said positioning means and said latch means thereon, said lever being pivotally movable in response to the pressure of a patient's finger against the finger rest held by said positioning means on the lever.

3. A lancet device according to claim 1 wherein: said finger rest has an opening which is outside said housing when the finger rest is held by said positioning means and which is positioned to pass the needle of the lancet needle assembly when said arm moves from said retracted position to said operating position in response to the pressure of a patient's finger against said finger rest around said opening therein on the opposite side of said finger rest from said holder on the arm.

4. A lancet device according to claim 3 wherein: said positioning means is pivoted in said housing and is movable pivotally in unison with said finger rest in response to the pressure of a patient's finger against said finger rest;

and said latch means is operably connected to said positioning means to release said arm from said retracted position upon said pivotal movement of said positioning means.

5. A lancet device according to claim 4 and having a pivoted lever which has both said positioning means and said latch means therein.

6. A lancet device comprising:

a housing;

an arm mounted in the housing for movement between a retracted position and an operating position, said arm having an end outside said housing:

a holder on said end of the arm, said holder having means for holding a lancet needle assembly with a needle for piercing a patient's finger:

and spring means urging said arm from said retracted position to said operating position;

a finger rest;

positioning means in said housing for holding said finger rest positioned on the outside of said housing in the path of said holder when said arm moves from said retracted position to said operating position, said positioning means being operable to permit movement of said finger rest with respect to said housing in response to the pressure of a patient's finger against the finger rest;

latch means in said housing for holding said arm in said retracted position against the urging of said spring means, said latch means being operable to release said arm from said retracted position in response to said movement of the finger rest;

said finger rest being manually insertable into and removable from said positioning means;

and means for preventing said latch means from releasing said arm except when said finger rest is in said positioning means.

7. A lancet device according to claim 2 and further comprising:

additional means for preventing said latch means from releasing said arm from said retracted position while said finger rest is in said positioning means, said additional means being manually operable to a position permitting said latch means to release said arm in response to said movement of the finger rest.

8. A lancet device comprising:

a housing;

an arm mounted in the housing for movement between a retracted position and an operating position, said arm having an end outside said housing;

a holder on said end of the arm, said holder having means for holding a lancet needle assembly with a needle for piercing a patient's finger;

spring means urging said arm from said retracted position to said operating position;

a finger rest;

positioning means in said housing for holding said finger rest positioned on the outside of said housing in the path of said holder when said arm moves from said retracted position to said operating position, said positioning means being operable to permit movement of said finger rest with respect to said housing in response to the pressure of a patient's finger against the finger rest;

latch means in said housing for holding said arm in said retracted position against the urging of said spring means, said latch means being operable to release said arm from said retracted position in response to said movement of the finger rest;

a pivoted lever having both said positioning means and said latch means thereon, said lever being pivotally movable in response to the pressure of a patient's finger against the finger rest held by said positioning means on the lever;

said finger rest being slidably insertable into and removable from said positioning means on said lever;

an ejector mounted on said housing for engagement with said lever to prevent pivotal movement of the lever in which said latch means on the lever releases said arm from said retracted position;

and an ejector lock arm holding said ejector engaging said lever and preventing said pivotal movement of the lever when said finger rest is not in said positioning means on the lever;

said finger rest when slidably inserted into said positioning means on the lever moving said ejector lock arm to a position releasing said ejector;

and said ejector when released by said ejector lock arm being movable on said housing to a position permitting said pivotal movement of the lever in response to pressure of the patient's finger on said finger rest.

9. A lancet device according to claim 8 and further comprising:

means on said ejector lock arm and said finger rest for locking said finger rest in said positioning means on the lever when said finger rest is fully inserted slidably into said positioning means.

10. A lancet device according to claim 6 and further comprising:

means on said ejector and said ejector lock arm for moving said ejector lock arm to release said finger rest from said positioning means in response to a predetermined movement of the ejector on the housing;

said ejector upon continuation of said movement engaging said finger rest and pushing said finger rest out of said positioning means on the lever.

11. A lancet device comprising:

a housing;

an arm mounted in the housing for movement between a retracted position and an operating position, said arm having an end outside said housing;

a holder on said end of the arm, said holder having means for holding a lancet needle assembly with a needle for piercing a patient's finger;

spring means urging said arm from said retracted position to said operating position;

a finger rest;

positioning means in said housing for holding said finger rest positioned on the outside of said housing in the path of said holder when said arm moves from said retracted position to said operating position, said positioning means being operable to permit movement of said finger rest with respect to said housing in response to the pressure of a patient's finger against the finger rest;

and latch means in said housing for holding said arm in said retracted position against the urging of said spring means, said latch means being operable to release said arm from said retracted position in response to said movement of the finger rest;

said finger rest having an opening which is outside said housing when the finger rest is held by said positioning means and which is positioned to pass the needle of the lancet needle assembly when said arm moves from said retracted position to said operating position in response to the pressure of a patient's finger against said finger rest around said opening therein on the opposite side of said finger rest from said holder on the arm;

said positioning means being pivoted in said housing and movable pivotally in unison with said finger rest in response to the pressure of a patient's finger against said finger rest;

said latch means being operably connected to said positioning means to release said arm from said retracted position upon said pivotal movement of said positioning means;

a pivoted lever having both said positioning means and said latch means thereon;

and said finger rest being slidably insertable into and removable from said positioning means on said lever.

12. A lancet device comprising:

a housing;

an arm mounted in the housing for movement between a retracted position and an operating position, said arm having an end outside said housing;

a holder on said end of the arm, said holder having means for holding a lancet needle assembly with a needle for piercing a patient's finger;

spring means urging said arm from said retracted position to said operating position;

a finger rest;

positioning means in said housing for holding said finger rest positioned on the outside of said housing in the path of said holder when said arm moves from said retracted position to said operating position, said positioning means being operable to permit movement of said finger rest with respect to said housing in response to the pressure of a patient's finger against the finger rest;

and latch means in said housing for holding said arm in said retracted position against the urging of said spring means, said latch means being operable to release said arm from said retracted position in response to said movement of the finger rest;

said finger rest having an opening which is outside said housing when the finger rest is held by said positioning means and which is positioned to pass the needle of the lancet needle assembly when said arm moves from said retracted position to said operating position in response to the pressure of a patient's finger against said finger rest around said opening therein on the opposite side of said finger rest from said holder on the arm;

said finger rest being slidably insertable into and removable from said positioning means.

13. In a lancet device having a housing:

an arm mounted in the housing for movement between a retracted position and an operating position, said arm having an end outside said housing;

a holder on said end of said housing, said holder having means for holding a lancet needle assembly including a needle for piercing a patient's finger;

and spring means urging said arm from said retracted position to said operating position; the improvement which comprises:

a pressure lever pivotally mounted inside said housing and having means for releasably holding said arm in said retracted position;

and a finger rest extending outside said housing in the path of movement of said holder when the arm moves form said retracted position to said operating position, said finger rest being operatively coupled to said lever to move the lever for releasing said arm from said retracted position in response to the pressure of a patient's finger against said finger rest.

14. A lancet device according to claim 13, wherein: said finger rest is operatively arranged to move said lever for releasing said arm in response to finger pressure against the opposite side of the finger rest from said holder on the arm;

and said finger rest has an opening for passing the needle to penetrate the patient's finger on said opposite side of the finger rest.

15. In a lancet device having
a housing:
an arm mounted in the housing for movement between a retracted position and an operating position, said arm having an end outside said housing;
a holder on said end of said housing, said holder having means for holding a lancet needle assembly including a needle for piercing a patient's finger;
and spring means urging said arm from said retracted position to said operating position; the improvement which comprises:
a pressure lever pivotally mounted inside said housing and having means for releasably holding said arm in said retracted position;
a finger rest extending outside said housing in the path of movement of said holder when the arm moves from said retracted position to said operating position, said finger rest being operatively coupled to said lever to move the lever for releasing said arm from said retracted position in response to the pressure of a patient's finger against said finger rest, said finger rest being manually insertable into said housing to be operatively coupled to said pressure lever;
and means for preventing the movement of the lever for releasing said arm until said finger rest is inserted into said housing.

16. A lancet device according to claim 15 wherein:
said lever has a front end outside said housing and a longitudinal slot which is open at said front end and extends rearward therefrom into said housing;
and said means for preventing the movement of the lever includes an ejector slidably mounted on said housing for displacement longitudinally of said lever, said ejector having an upper end segment slidable along said slot in the lever, said upper end segment of the ejector overlying the bottom of said slot in the lever in forward positions of the ejector along the lever, whereby said ejector in said forward positions prevents pivotal movement of the lever for releasing said arm from said retracted position, said upper end segment of the ejector in rearward position of the ejector along the lever permitting pivotal movement of the lever for releasing said arm from said retracted position.

17. A lancet device according to claim 16 and further comprising:
an ejector lock bar in said housing behind said ejector, said ejector lock bar being slidable longitudinally of said lever between a forward position and a rearward position, said ejector lock bar having means thereon for holding said arm in said retracted position when the ejector lock bar in its forward position
said ejector being manually slidable rearward along said lever to push said ejector lock bar from its forward position to its rearward position releasing it from said arm and to disengage said upper end segment of the ejector from said bottom of the slot in the lever, whereby to permit the lever to be moved pivotally by the pressure of a patient's finger against said finger rest, whereby to release said arm from said retracted position.

18. A lancet device according to claim 16 and further comprising:
an ejector lock arm pivotally mounted in said housing above said lever and said ejector, said ejector lock arm having means for preventing movement of the ejector to said rearward positions when said ejector lock arm is in a lowered position;
and spring means biasing said ejector lock arm to said lowered position;
said finger pad when inserted into housing pivoting said ejector lock arm upward to release said ejector for movement to said rearward positions and thereafter pushing said ejector rearward along said lever.

19. In a lancet device having
a housing:
an arm mounted in the housing for movement between a retracted position and an operating position, said arm having an end outside said housing;
a holder on said end of said housing, said holder having means for holding a lancet needle assembly including a needle for piercing a patient's finger;
and spring means urging said arm from said retracted position to said operating position; the improvement which comprises:
a horizontally elongated pressure lever pivotally mounted inside said housing, said lever having a front end outside said housing and a longitudinal slot which is open at said front end and extends rearward therefrom into said housing, said lever having an upwardly extending transverse end segment on its back end inside said housing;
an ejector slidably mounted on said housing for displacement longitudinally of said lever, said ejector having an upper end segment slidable along said slot in the lever, said upper end segment of the ejector overlying the bottom of said slot in the lever in forward positions of the ejector along the lever, whereby said ejector in said forward positions prevents pivotal movement of the lever, said upper end segment of the ejector in rearward positions of the ejector along the lever permitting pivotal movement of the lever upward at said front end;
an ejector lock bar in said housing behind said ejector, said ejector lock bar being slidable longitudinally of said lever between a forward position and a rearward position, said ejector lock bar having an upwardly extending transverse end segment on its back end which extends even with said upwardly extending transverse end segment of the lever in said forward position of the ejector lock bar;
an ejector lock arm pivotally mounted in said housing above said lever and said ejector, said ejector lock arm having means for preventing movement of the ejector to said rearward positions when said ejector lock arm is in a lowered position;
spring means biasing said ejector lock arm to said lowered position;
a finger rest slidably insertable into and removable from said slot in the lever from in front of the housing, said finger rest when inserted into said slot pivoting said ejector lock arm upward to release said ejector for movement to said rearward positions and thereafter pushing said ejector rearward along said slot and into engagement with said ejector lock bar, said finger rest having an opening which is outside said housing when the finger rest is fully inserted in said slot in the lever and which is positioned to pass the needle of the lancet needle assembly when said arm moves from said retracted position to said operating position;

said ejector being manually slidable rearward along said lever to push said ejector lock bar from its forward position to its rearward position and to disengage said upper end segment of the ejector from said bottom of the slot in the lever, whereby to permit the lever to be moved pivotally upward at its front end by the upward pressure of a patient's finger against said finger rest;

said upwardly extending end segments of the lever and the ejector lock bar holding said arm in its retracted position when the front end of the lever is down and the ejector lock bar is in its forward position, said upwardly extending end segment of the ejector lock bar releasing said arm when the ejector lock bar is pushed back to its rearward position by said ejector, and said upwardly extending end segment of the lever releasing said arm when the front end of the lever is moved up with the finger rest by the patient's finger;

and said ejector being slidable forward along the housing, after said arm has moved from said retracted position to said operating position, to push said finger rest forward out of said lever.

* * * * *